US008197459B2

(12) United States Patent
Jansen et al.

(10) Patent No.: US 8,197,459 B2
(45) Date of Patent: Jun. 12, 2012

(54) SELF-SEALING MEDICAL FLUID TRANSFER DEVICE

(75) Inventors: Hubert Jansen, Stolberg (DE); Uwe Wortmann, Marburg (DE)

(73) Assignee: Aventis Behring GmbH, Marburg (DE)

( * ) Notice: Subject to any disclaimer, the term of this patent is extended or adjusted under 35 U.S.C. 154(b) by 219 days.

(21) Appl. No.: 10/791,869

(22) Filed: Mar. 4, 2004

(65) Prior Publication Data

US 2004/0236305 A1 Nov. 25, 2004

(30) Foreign Application Priority Data

Mar. 5, 2003 (DE) .................................. 103 09 796

(51) Int. Cl.
*A61B 19/00* (2006.01)
*A61M 5/32* (2006.01)

(52) U.S. Cl. ........................................ 604/411; 604/414

(58) Field of Classification Search .................. 604/533, 604/905, 403–416; 206/363–366; 215/247–249; 222/188
See application file for complete search history.

(56) References Cited

U.S. PATENT DOCUMENTS 3,977,555 A * 8/1976 Larson .......................... 215/247
4,423,741 A 1/1984 Levy
4,883,483 A 11/1989 Lindmayer
5,211,638 A * 5/1993 Dudar et al. .................. 604/539
5,358,501 A * 10/1994 Meyer ........................... 604/414
5,374,264 A * 12/1994 Wadsworth, Jr. ............. 604/414
5,454,409 A * 10/1995 McAffer et al. .............. 141/329
5,454,805 A * 10/1995 Brony ........................... 604/406
5,833,213 A 11/1998 Ryan
5,895,383 A * 4/1999 Niedospial, Jr. .............. 604/403
5,971,021 A 10/1999 Graham
5,996,811 A 12/1999 Kitajima et al.
6,022,339 A 2/2000 Fowles et al.
6,238,372 B1 * 5/2001 Zinger et al. .................. 604/246
6,240,960 B1 6/2001 Fillmore
6,355,023 B1 3/2002 Roth et al.
6,558,365 B2 * 5/2003 Zinger et al. .................. 604/410

(Continued)

FOREIGN PATENT DOCUMENTS

DE 690 03 805 T2 5/1994

(Continued)

OTHER PUBLICATIONS

Japanese Office Action regarding Japanese Patent Appln No. 2004-60169 mailed Jul. 21, 2009. (4 pgs.).

(Continued)

*Primary Examiner* — Tatyana Zalukaeva
*Assistant Examiner* — Philip R Wiest
(74) *Attorney, Agent, or Firm* — Finnegan, Henderson, Farabow, Garrett & Dunner, LLP

(57) ABSTRACT

Embodiments of the invention relate to a transfer device for a container whose interior is under negative pressure and which is closed by means of an elastic stopper. The device has a receiving cap and a piercing mandril for piercing the stopper. Relative to its direction of piercing, the piercing mandril is provided with a front piercing portion and with a rear sealing portion which is of greater diameter. In the position in which a bead of the container is inserted into the receiving cap, the sealing portion contacts the stopper. In this way, a tear in the stopper, which tear has been formed by eccentric application of the device onto the container, can be sealed off.

13 Claims, 4 Drawing Sheets

U.S. PATENT DOCUMENTS

Figure 1:
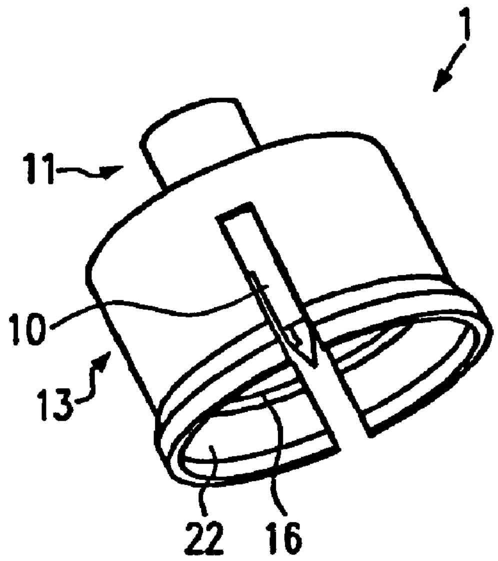

| | | | | |
|---|---|---|---|---|
| 6,578,576 | B1 * | 6/2003 | Taormina et al. | 128/207.17 |
| 2001/0025672 | A1 | 10/2001 | Thibault et al. | |
| 2001/0029360 | A1 | 10/2001 | Miyoshi et al. | |
| 2002/0087141 | A1 | 7/2002 | Zinger et al. | |
| 2002/0121496 | A1 * | 9/2002 | Thiebault et al. | 215/249 |

FOREIGN PATENT DOCUMENTS

| | | | |
|---|---|---|---|
| DE | 196 03 632 | A1 | 8/1997 |
| DE | 100 57 153 | A1 | 11/2000 |
| EP | 0 521 460 | B1 | 1/1993 |
| EP | 0 635 253 | A1 | 1/1995 |
| EP | 0 499 481 | B1 | 12/1996 |
| EP | 1 145 702 | A2 | 10/2001 |
| JP | 10-225448 | | 8/1998 |
| WO | 97/20536 | | 6/1997 |
| WO | 99/08036 | | 2/1999 |
| WO | 02/45649 | A1 | 6/2002 |

OTHER PUBLICATIONS

Translation of Japanese Office Action regarding Japanese Patent Appln No. 2004-60169 mailed Jul. 21, 2009. (4 pgs.).

Canadian Office Action regarding Canadian Patent Appln No. 2,459,644 mailed May 31, 2010. (3 pgs.).

Canadian Office Action regarding Canadian Patent Appln No. 2,459,644 mailed Mar. 25, 2011. (2 pgs.).

* cited by examiner

SELF-SEALING MEDICAL FLUID TRANSFER DEVICE

This application claims the benefits of priority under 35 U.S.C. §119(a)-(d) to German Patent Application No. 10309796.1 which was filed in the German Patent Office on Mar. 5, 2003, the entirety of which is incorporated herein by reference.

The invention relates to a transfer device, in particular for a container under negative pressure, with a receiving cap for receiving a bead of the container closed by means of an elastic stopper, the receiving cap having an edge portion for centering the bead in its position of insertion in the receiving cap, and a lid portion, and with a central piercing mandril which is connected to the lid portion and projects into the space enclosed by the receiving cap, the piercing mandril piercing the stopper when the bead is inserted into the receiving cap, and the piercing mandril having a flow channel extending through it for a fluid which is conveyed outward through the lid portion.

A transfer device of this kind is known from, for example, U.S. 2002/00 87 141 A1. In the latter, the piercing mandril has a constant external diameter, except for its pointed end.

Particularly in transfer devices in which a fluid is to be conveyed into the container under negative pressure, for example in order to dissolve a medical substance with the aid of a medical fluid, it is important that the piercing mandril pushed into the elastic stopper is sealed with respect to the stopper. Only in this way can the negative pressure in the container be maintained. This is necessary in order to draw the fluid into the container by suction. In the event of a preliminary pressure compensation in the container, only an inadequate amount of the fluid gets into the container. The mixing ratio is therefore incorrect, and for this reason the content of the container has to be discarded.

The containers used in connection with such transfer devices are generally designed as glass vials.

In such transfer devices, when the container is inserted into the transfer device, the pointed end of the piercing mandril comes into contact with the stopper before the edge portion of the receiving cap contacts the bead of the container and can thus center the bead and consequently the stopper relative to the piercing mandril. With the eccentric positioning of the stopper relative to the tip of the piercing mandril, the insertion movement, and thus the guiding of the bead of the container by means of the edge portion of the receiving cap, has the effect that the piercing mandril inserted eccentrically into the stopper is now moved into its central position. The result of this is a tear in the rubber, which tear reaches from the site of application of the piercing mandril to the center of the stopper. The piercing mandril, which has a constant diameter, is not suitable for sealing this tear. As a consequence of this, the described leakage occurs.

The object of the present invention is to develop a transfer device of the type mentioned at the outset in such a way that, with the stopper pierced, a fluid-tight contact between piercing mandril and stopper is guaranteed even when the piercing mandril has been applied eccentrically to the stopper.

In a transfer device of the type mentioned at the outset, the object is achieved by the fact that, relative to its direction of piercing, the piercing mandril has a front piercing portion and a rear sealing portion which is of greater diameter, and, in the position in which the bead is inserted into the receiving cap, the sealing portion contacts the stopper.

Thus, in addition to the piercing portion which has the function of piercing the stopper, a sealing portion, to the rear in the direction of piercing, is provided which seals off the tear which has formed in the stopper upon eccentric application of the transfer device to the stopper. As a consequence, the piercing mandril pierces the stopper in a sealing manner, so that leakage is prevented.

Advantageously, the diameter of the piercing portion is relatively small, it being entirely possible for this to be of needle thickness.

The transfer device is preferably made of plastic, in particular as an injection-molded part. In this connection, it is considered particularly advantageous if the transfer device is of a substantially rotationally symmetrical design. In this configuration and type of production, the edge of the receiving cap can advantageously be designed with an inward projection which engages behind the bead in the position of insertion of the bead in the receiving cap. To precisely center the piercing mandril relative to the stopper, the axial distance between inward projection and sealing portion should be smaller than the axial distance between inward projection and that surface of the stopper facing the lid when the bead is in the position of insertion in the receiving cap.

The piercing mandril can be configured in different ways in order to guarantee the sealing; provided for according to the invention, of the tear in the stopper.

In an advantageous embodiment of the piercing mandril, the transition from the piercing portion to the sealing portion of the piercing mandril is stepped, the end face of the sealing portion of the piercing mandril making annular contact with the stopper. Because of the advantageously selected pairing of materials, on the one hand the design of the transfer device with the piercing mandril made of plastic, and on the other hand the elastic stopper, a preferred refinement is one in which a sealing element is integrated into the end face of the sealing portion. This is, for example, an elastic component, preferably an O-ring. The sealing thus takes place between two elastic parts.

The length of the sealing portion is in particular dimensioned such that the sealing portion penetrates into the stopper when the bead is in its position of insertion in the receiving cap. The stopper is thus sealed under a certain pretensioning, with the result that the tear formed in the stopper is pressed together under the action of the pressure forces of the piercing mandril on the stopper.

According to another advantageous embodiment, it is provided that the piercing portion widens conically toward the sealing portion. The tear in the stopper is thus sealed on account of the conicity of the sealing portion. In this case, the sealing portion can be a conical widening which directly adjoins the piercing portion. The entire piercing mandril is therefore of conical design. It is equally conceivable for the piercing mandril to have a stepped design in which the conically widening sealing portion adjoins the step between piercing portion and sealing portion. The tear in the stopper is in this case sealed via the conical surface of the sealing portion. In principle, it is possible for a wider area of the sealing portion to adjoin the conical sealing portion in a stepped manner. In this case, the stopper is on the one hand sealed radially via the conical area of the sealing portion and on the other hand sealed axially by the adjoining stepped area of the sealing portion.

Further features of the invention are set out in the description of the figures, and in the figures themselves.

Figure 2:
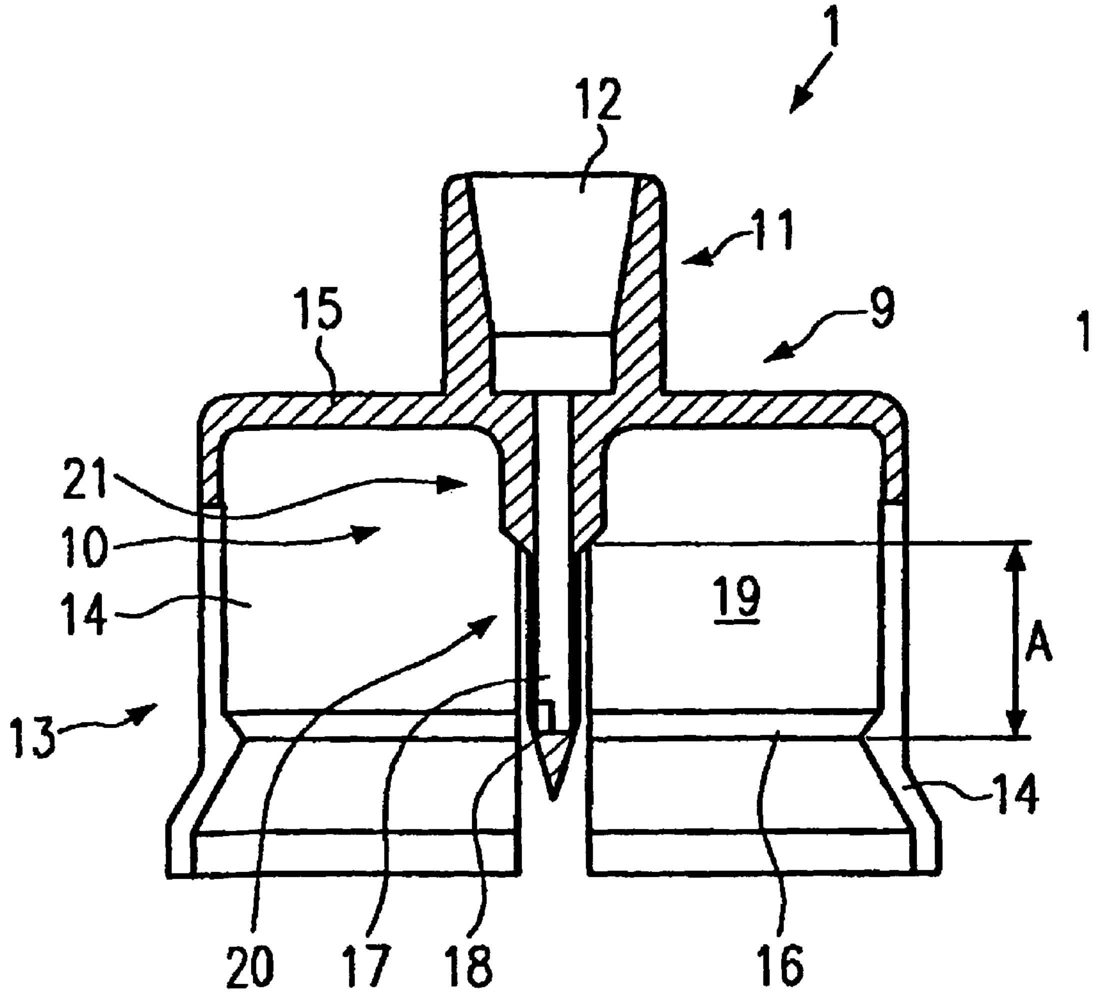
Figure 3:
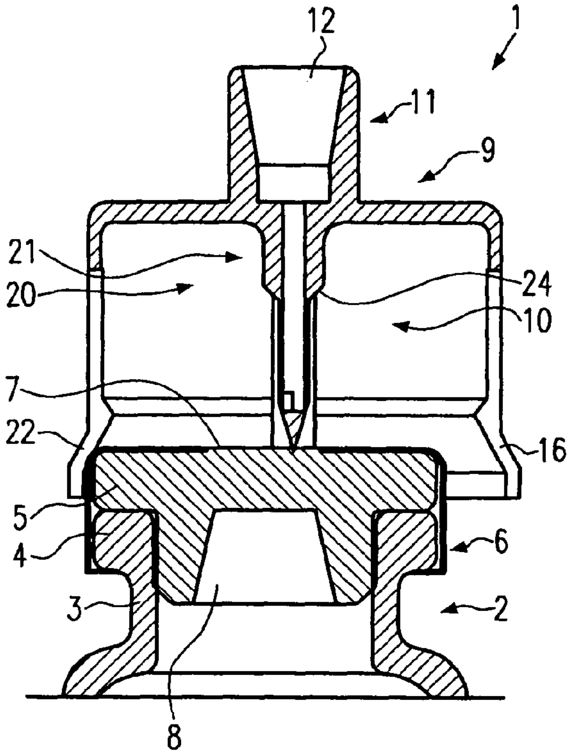
Figure 4:
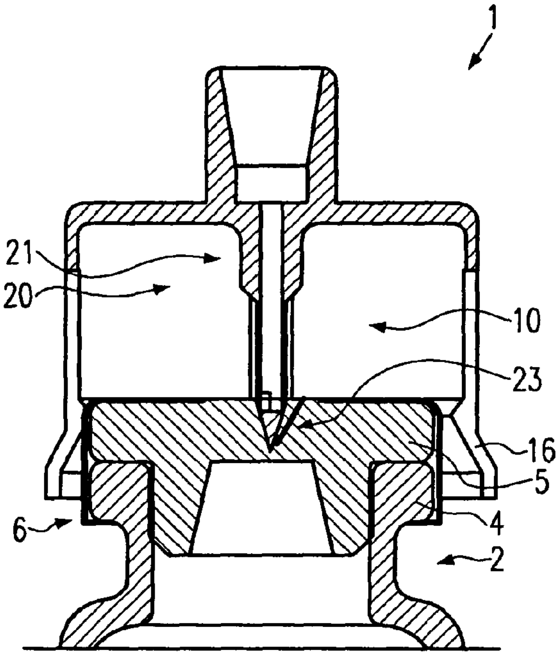
Figure 5:
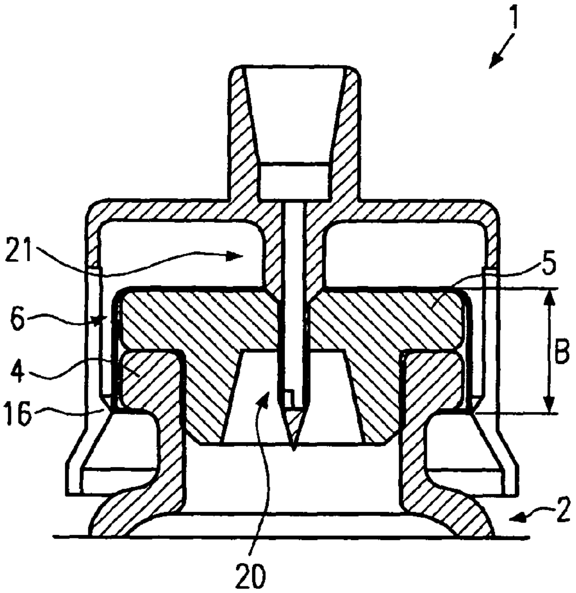
Figure 6:
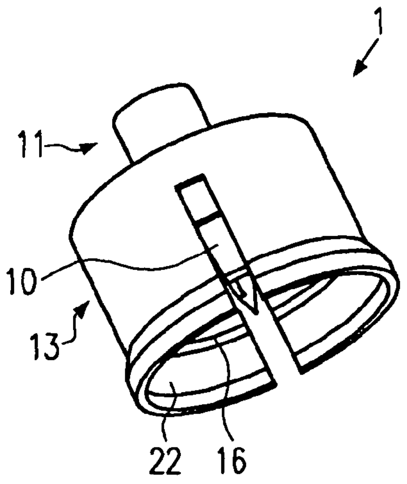
Figure 7:
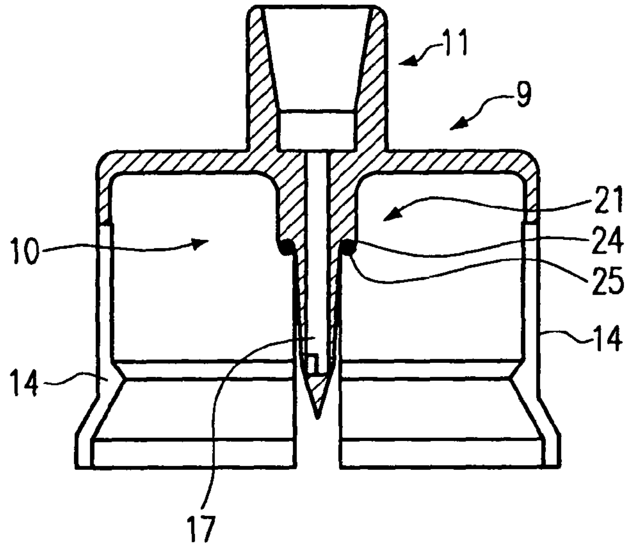
Figure 8:
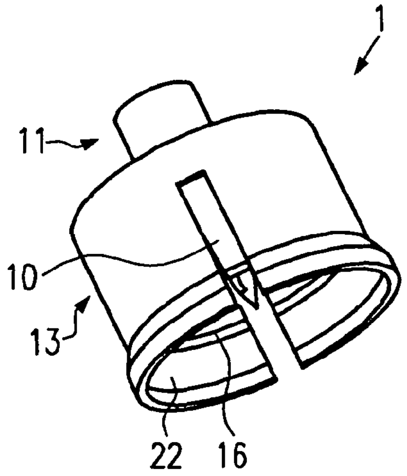
Figure 9:
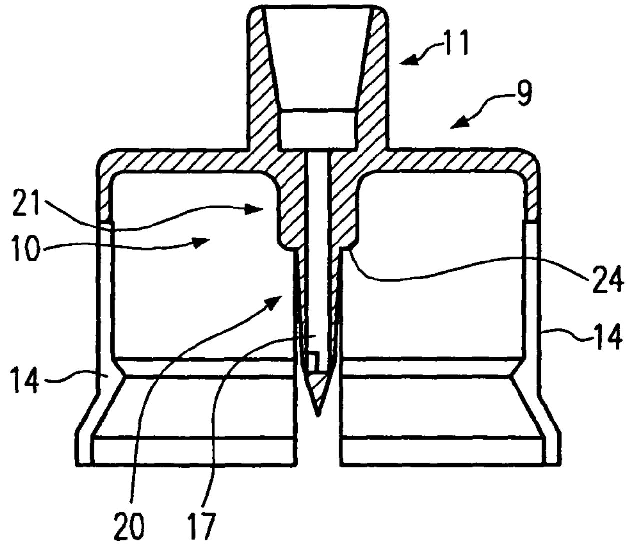

In the figures in the drawing, the invention is depicted on the basis of a number of illustrative embodiments, without being limited thereto. In the drawing:

FIG. 1 shows a perspective view of a first illustrative embodiment of the transfer device according to the invention, seen obliquely from below, FIG. 2 shows a longitudinal central section through the transfer device shown in FIG. 1, FIG. 3 shows, in a longitudinal central section, the transfer device according to FIGS. 1 and 2 at the moment of its eccentric application to the stopper fitted in a glass vial, FIG. 4 shows a cross-sectional representation of the arrangement according to FIG. 3, with the piercing mandril centered and inserted into the stopper, FIG. 5 shows a cross-sectional representation of the arrangement according to FIGS. 3 and 4, with the transfer device applied fully to the glass vial, FIG. 6 shows a perspective view of a second illustrative-embodiment of the transfer device, seen obliquely from below, FIG. 7 shows the transfer device according to FIG. 6, in a longitudinal central section, FIG. 8 shows a perspective view of a third illustrative embodiment of the transfer device, seen obliquely from below, FIG. 9 shows the transfer device according to FIG. 8 in a longitudinal central section.

The transfer device 1 according to the first illustrative embodiment shown in FIGS. 1 through 5 is produced as an injection-molded plastic part. It is used in particular for a container whose interior is under negative pressure and which is designed as a glass vial 2.

Adjacent to its neck 3, the glass vial 2 has a bead 4 into which an elastic stopper 5 is inserted. The external diameter of the stopper 5 corresponds to that of the bead 4. The stopper 5 is held securely in the bead 4 by means of a thin-walled cap 6 which surrounds the stopper 5 and the bead 4, except for a central opening 7 in the cap 6 in the area of the axis of symmetry of cap 6 and glass vial 2. The area of the stopper 5 inserted into the glass vial 2 is of annular design so that, directed toward the interior of the glass vial 2, a recess 8 is formed in the stopper 5. In this area, the stopper 5 has a thickness corresponding to that of the stopper in the area of the outer edge.

The transfer device 1 is formed by a receiving cap 9, a piercing mandril 10 and a connector piece 11. The connector piece 11 is provided with a conically tapering recess 12 which serves to receive, for example, the syringe cone of a disposable syringe. Moreover, the connector piece 11 is suitable for receiving another complementary transfer device in a sealed manner, for example as is described in U.S. 2002/0087,141 A1 in respect of the basic design and use of the transfer device. In this case, the whole device serves for transferring a medical fluid, which is located in a first glass vial, into a second glass vial, in the present case the glass vial 2, which is under negative pressure and in which, for example, there is a medical substance which is to be dissolved. After this substance has dissolved, the other transfer device is separated from the transfer device 1, and, after the vial 2 has been turned upside down, the disposable syringe inserted into the connector piece 11 can be used to removed the dissolved substance from this vial.

The receiving cap 9 of the transfer device 1 has an edge portion 13 for centering the bead 4 in its position of insertion in the receiving cap 9. The edge portion 13 is provided axially with four tabs 14 which each extend over a sector of 90° and are mounted so as to yield radially with respect to a lid portion 15 adjacent to the edge portions 13 of the receiving cap 9, so that they can spring outward when the glass vial 2 is inserted into the transfer device 1. The edge portion 13 is provided with an inwardly directed projection 16. The latter engages behind the bead 4 of the vial 2 in the bead's position of insertion in the receiving cap 9 (as is illustrated in FIG. 5). This inward projection 16 is arranged parallel to the plate-shaped lid portion 15.

In the rotationally symmetrical transfer device 1, the piercing mandril 10 is connected to the lid portion 15. Its end directed away from the lid portion 15 is pointed. A flow channel 17 extending through the piercing mandril 10 is provided with radial openings 18 in the area of the tip of the piercing mandril 10, and it is connected at its other end to the recess 12. The piercing mandril 10 thus projects into the space 19 enclosed by the receiving cap 9.

Relative to its direction of piercing, the piercing mandril 10 has a front piercing portion 20 and a rear sealing portion 21 which is of greater diameter. The transition from the piercing portion 20 to the sealing portion 21 is stepped. The length of the sealing portion 21 is dimensioned such that it penetrates into the stopper 5 when the bead 4 is in its position of insertion in the receiving cap 9. This is due to the axial distance A between inward projection 16 and sealing portion 21 being smaller than the axial distance B between inward projection 16 and that surface of the stopper 5 facing the lid portion 15, when the bead 4 is in its position of insertion in the receiving cap 9.

The details explained above can be taken from FIGS. 3 through 5 which illustrate the procedure for inserting the glass vial 2 into the transfer device 1: FIG. 3 shows the transfer device 1 applied with the tip of the piercing mandril 10 eccentrically to the stopper 5. At this moment, the geometry of the transfer device 1 means that the inward projection 16 used for centering is not yet in contact with the stopper 5 or the cap 6 surrounding this. Instead, the transfer device 1 lies on the cap 6 via a conically tapering insertion bevel 22 of the edge portion 13 along a short line or a punctiform contact. When the glass vial 2 is inserted farther into the transfer device 1, as is illustrated in FIG. 4, the insertion bevel 22 and the inward projection 16 ensure that the glass vial 2 with the stopper 5 is centered with respect to the transfer device 1. Since the axial piercing movement of the piercing mandril 10 is superposed by a radial movement, a tear 23 forms in the elastic stopper 5 during piercing of the stopper 5, which is designed in particular as a rubber stopper. When the glass vial 2 is pushed farther into the transfer device 1 until the inward projection 16 engages behind the cap 6 in the area of the bead 4 of the glass vial, the sealing portion 21 of the piercing mandril 10 is in a position relative to the stopper 5 in which it not only touches the latter but in which its end face is forced into the stopper 5. The end face 24 of the sealing portion 21 thus contacts the stopper 5 in an annular formation. The stepped formation between sealing portion 21 and piercing portion 20 is chosen such that, when the glass vial 2 is inserted fully into the transfer device 1 as is shown in FIG. 5, the tear 23 is sealed off by the sealing portion 21.

The embodiment according to FIGS. 6 and 7 differs from that according to FIGS. 1 through 5 in that an O-ring 25 is fitted into the end face 24 of the sealing portion 21. In this embodiment, the elastic O-ring 25 thus contacts the elastic stopper 5, in contrast to the embodiment according to FIGS. 1 through 5 in which the elastic stopper 5 is contacted by the nonelastic sealing portion 21.

The embodiment according to FIGS. 8 and 9 differs from that according to FIGS. 1 through 5 in that the piercing portion 20 widens conically starting from the tip of the piercing mandril 10. Upon insertion of the glass vial 2 into the transfer device 1 in the sense of the functional representation according to FIGS. 3 through 5, a certain sealing effect in the area of the tear 23 is already achieved by means of the conically shaped piercing portion 20 when the piercing mandril 10 penetrates into the stopper 5. When the glass vial 2 is in the position in which it has been inserted fully into the transfer device 1, additional sealing is afforded via the end face 24 of the sealing portion 21.

Alternatively, in the embodiment according to FIGS. 8 and 9 the dimensions can be such that, in the assembly position according to FIG. 5, the portion 21 does not contact the stopper 5, and instead the conically shaped portion 20 performs both the function of the piercing portion and that of the sealing portion. The sealing is thus achieved exclusively as a result of the radial action of the portion 20 on the stopper 5, specifically the tear 23 in the stopper 5.

LIST OF REFERENCE NUMBERS 1 transfer device
2 glass vial
3 neck of vial
4 bead
5 stopper
6 cap.
7 opening
8 recess
9 receiving cap
10 piercing mandril
11 connector piece
12 recess
13 edge portion
14 tab
15 lid portion
16 inward projection
17 flow channel
18 opening
19 space
20 piercing portion
21 sealing portion
22 insertion bevel
23 tear
24 end face
25 O-ring

The invention claimed is:

1. A plastic fluid transfer device, comprising:
a lid portion;
an edge portion formed integrally with the lid portion, the edge portion and lid portion defining a space for receiving a bead of a container closed by an elastic stopper; and
a piercing mandrel formed integrally with and extending from the lid portion,
the piercing mandrel including a piercing portion configured to pierce completely through a thickness of the elastic stopper from an external surface of the elastic stopper outside the container to an internal surface of the elastic stopper inside the container as the bead is received in the space, the piercing portion including a pointed end and a cylindrical portion of constant diameter,
the piercing mandrel further including a sealing portion having a first portion adjoining the cylindrical portion and a second portion extending from the first portion to a position proximate the lid portion, wherein the first portion is sloped from the cylindrical portion to the second portion so as to form an acute angle with respect to a longitudinal axis of the piercing mandrel, and wherein the first portion of the sealing portion is configured to be disposed between the external surface of the elastic stopper and the internal surface of the elastic stopper when the piercing mandrel pierces completely through the thickness of the elastic stopper, and the first portion of the sealing portion being configured to seal a tear in the thickness of the elastic stopper formed upon eccentric application of the fluid transfer device to the elastic stopper.

2. The fluid transfer device of claim 1, wherein the edge portion includes an inward projection configures to center the bead as the bead is received within the space.

3. The fluid transfer device of claim 2, wherein the inward projection is further configured to engage a behind portion of the bead when the bead is substantially disposed in the space.

4. The fluid transfer device of claim 3, wherein a first axial distance between the inward projection and the sealing portion is less than a second axial distance between the inward projection and a surface of the elastic stopper facing the lid portion when the bead is substantially in the space.

5. The fluid transfer device of claim 3, wherein the sealing portion is configured to contact the elastic stopper substantially at the same time as when the inward projection engages with the behind portion of the bead.

6. The fluid transfer device of claim 2, wherein the inward projection is disposed radially around the piercing mandrel even before the piercing portion pierces the elastic stopper.

7. The fluid transfer device of claim 2, wherein the piercing portion is disposed further away from the lid portion than the inward projection.

8. The fluid transfer device of claim 2, wherein a portion of the edge portion extends away from both the lid portion and the inward projection.

9. The fluid transfer device of claim 2, wherein the edge portion includes a free edge extending away from the inward projection at least partly along a direction substantially parallel to a central longitudinal axis of the space.

10. The fluid transfer device of claim 9, wherein the free edge has an outer diameter larger than an outer diameter of both the inward projection and a portion of the edge portion between the inward projection and the lid portion.

11. The fluid transfer device of claim 9, wherein the free edge has an inner diameter larger than an outer diameter of both the inward projection and a portion of the edge portion between the inward projection and the lid portion.

12. The fluid transfer device of claim 1, wherein the piercing mandrel is stationary relative to the lid portion when the piercing portion pierces the elastic stopper.

13. A plastic fluid transfer device, comprising:
a lid portion;
an edge portion formed integrally with the lid portion, the edge portion and lid portion defining a space for receiving a bead of a container closed by an elastic stopper; and
a piercing mandrel formed integrally with and extending from the lid portion,
the piercing mandrel including a piercing portion configured to pierce completely through a thickness of the elastic stopper from an external surface of the elastic stopper outside the container to an internal surface of the elastic stopper inside the container as the bead is received in the space, the piercing portion including a pointed end and a cylindrical portion of constant diameter,
the piercing mandrel further including a sealing portion having a first portion adjoining the cylindrical portion and widening to a second portion which extends from the first portion towards the lid portion, the first portion of the sealing portion being configured to seal a tear in the thickness of the elastic stopper formed upon eccentric application of the fluid transfer device to the elastic stopper, wherein the sealing portion of the piercing mandrel is configured to penetrate the elastic stopper when the bead is substantially disposed in the space, and wherein the first portion of the sealing portion is configured to be disposed between the external surface of the elastic stopper and the internal surface of the elastic stopper when the piercing mandrel pierces completely through the thickness of the elastic stopper.

* * * * *

UNITED STATES PATENT AND TRADEMARK OFFICE

CERTIFICATE OF CORRECTION

PATENT NO. : 8,197,459 B2
APPLICATION NO. : 10/791869
DATED : June 12, 2012
INVENTOR(S) : Hubert Jansen et al.

It is certified that error appears in the above-identified patent and that said Letters Patent is hereby corrected as shown below:

In claim 2, column 6, line 7, “configures to center” should read --configured to center--.

Signed and Sealed this
Twenty-third Day of October, 2012

David J. Kappos
*Director of the United States Patent and Trademark Office*